United States Patent [19]

Suzuki et al.

[11] 4,204,070

[45] May 20, 1980

[54] PROCESS FOR PREPARING POLYETHYLENE TEREPHTHALATE AND ITS LOW MOLECULAR WEIGHT OLIGOMERS

[75] Inventors: Fumiyuki Suzuki; Toshimitu Okutu; Keitaro Ohe, all of Minami-ashigara, Japan

[73] Assignee: Fuji Photo Film Co., Ltd., Kanagawa, Japan

[21] Appl. No.: 679,612

[22] Filed: Apr. 23, 1976

[30] Foreign Application Priority Data

Apr. 23, 1975 [JP] Japan ................................. 50-49350

[51] Int. Cl.² ............................................. C07C 69/82
[52] U.S. Cl. ...................................... 560/94; 528/309
[58] Field of Search ........................ 260/475 P; 560/94

[56] References Cited

U.S. PATENT DOCUMENTS 3,639,448  2/1972  Matsuzawa et a. ............... 260/475 P

FOREIGN PATENT DOCUMENTS 39-23564 10/1964 Japan ................................... 260/475 P
40-28295 12/1965 Japan ................................... 260/475 P
48-94795 12/1973 Japan .

*Primary Examiner*—Jane S. Myers
*Attorney, Agent, or Firm*—Sughrue, Rothwell, Mion, Zinn and Macpeak

[57] ABSTRACT

A process for preparing bis(hydroxyethyl)terephthalate and its low molecular weight oligomers in a reactor equipped with a rectifying column which comprises suspending or dissolving terephthalic acid in molten bis(hydroxyethyl)terephthalate and its low molecular weight oligomers at a temperature above the dew point of ethylene glycol and feeding gaseous or liquid ethylene glycol into the suspension or the solution to react it with the terephthalic acid, where the amount of ethylene glycol fed into the reactor is controlled so as to maintain the temperature inside the rectifying column at a temperature at which the ethylene glycol does not substantially distill off from the rectifying column and the partial pressure of the ethylene glycol is maximized.

6 Claims, 3 Drawing Figures

PROCESS FOR PREPARING POLYETHYLENE TEREPHTHALATE AND ITS LOW MOLECULAR WEIGHT OLIGOMERS

BACKGROUND OF THE INVENTION

1. Field of the Invention

This invention relates to a process for preparing polyethylene terephthalate and its low molecular weight oligomers. More specifically, it relates to a process for preparing bis-(hydroxyethyl) terephthalate and its low molecular weight oligomers (hereinafter both of these will be referred to as "BHET") by the direct reaction of terephthalic acid and ethylene glycol.

2. Description of the Prior Art

Methods for preparing BHET by directly reacting terephthalic acid and ethylene glycol are known. Since terephthalic acid is not compatible with ethylene glycol, the reaction system is a solid-liquid heterogeneous system. When ethylene glycol is used in a relatively small proportion as compared with terephthalic acid, for example, in a proportion of not more than 2 moles per mole of terephthalic acid, the terephthalic acid becomes a wet mass or a slurry due to the effect of the liquid ethylene glycol and heat transmission is reduced. Consequently, a long period of time is required to elevate the temperature of the reaction system, and overheating occurs locally to cause undesirable side reactions. On the other hand, when the reaction is carried out using a large excess (e.g., more than 4 moles) of ethylene glycol, the flowability of the reaction system is improved, but another difficulty arises in that by-product diethylene glycol is formed in large quantities to lower the melting point of polyethylene terephthalate final product and deteriorate its thermal stability.

In an attempt to overcome these difficulties, Japanese Patent Publication 8915/57 discloses a method in which BHET is added in addition to terephthalic acid and ethylene glycol so that the flowability of the reaction system is improved by the melting of this oligomer. However, by this method side reactions are not sufficiently inhibited.

Japanese Pat. Publication No. 22463/71, on the other hand, discloses a method which comprises suspending or dissolving terephthalic acid in molten BHET, maintaining the suspension or solution at a temperature above the dew point of ethylene glycol, and feeding gaseous or liquid ethylene glycol into the suspension or solution to react it with terephthalic acid. Since a large quantity of ethylene glycol is fed in this method, the amount of ethylene glycol that distills off is large. Usually, the ethylene glycol that distills off contains diethylene glycol, terephthalic acid, BHET, mono-(hydroxyethyl) terephthalate, etc., and for the re-use of this ethylene glycol, it must be subjected to a purifying process such as distillation. In commercial operation, the equipment for this purpose is naturally of large scale, which results in increased production costs. In addition, thermal losses are high since it is necessary to gasify ethylene glycol in an amount greater than the stoichiometrical amount required for the reaction.

Japanese Patent Application (OPI) No. 94795/73 discloses a method in which the operating temperature is limited in order to more efficiently carry out the reaction shown in Japanese Patent Publication No. 22463/71. The method involves maintaining BHET at its boiling point in an equilibrium state at its average degree of polymerization, suspending or dissolving terephthalic acid in the BHET, and then adding ethylene glycol while controlling the amount added so that the boiling point of the reaction system can be maintained at the above mentioned temperature. This method makes it possible to shorten the reaction time and reduce the amount of by-product diethylene glycol. However, since no temperature control is exercised in a rectifying column, the distilling off of ethylene glycol cannot be completely prevented. Thus, as in the previously cited method, a purifying process is required, and this method is also not free from economic disadvantages.

SUMMARY OF THE INVENTION

Accordingly, it is one object of this invention to provide a process for preparing BHET in which the amount of ethylene glycol consumed can be reduced to the stoichiometrically required amount.

Another object of this invention is to provide a process for preparing BHET at a high rate of reaction.

A further object of this invention is to provide a process for preparing BHET which does not require equipment for recovering and purifying ethylene glycol.

Still another object of this invention is to provide a process for preparing BHET wherein thermal losses are small.

Yet another object of this invention is to provide a process for preparing BHET which involves lowered waste disposal.

In order to reach these objects, we made extensive investigations into a method which comprises suspending or dissolving terephthalic acid in molten BHET at a temperature above the dew point of ethylene glycol, and feeding gaseous or liquid ethylene glycol into the suspension or the solution to react it with terephthalic acid. These investigations led to the discovery that the amount of ethylene glycol consumed can be reduced to the stoichiometrically required amount and the rate of reaction can be increased by controlling the amount of ethylene glycol fed to the reactor so that the temperature inside a rectifying column is maintained at a temperature at which ethylene glycol does not substantially distill off from the top of the rectifying column and the partial pressure of ethylene glycol is maximized.

DETAILED DESCRIPTION OF THE INVENTION

Figure 1:
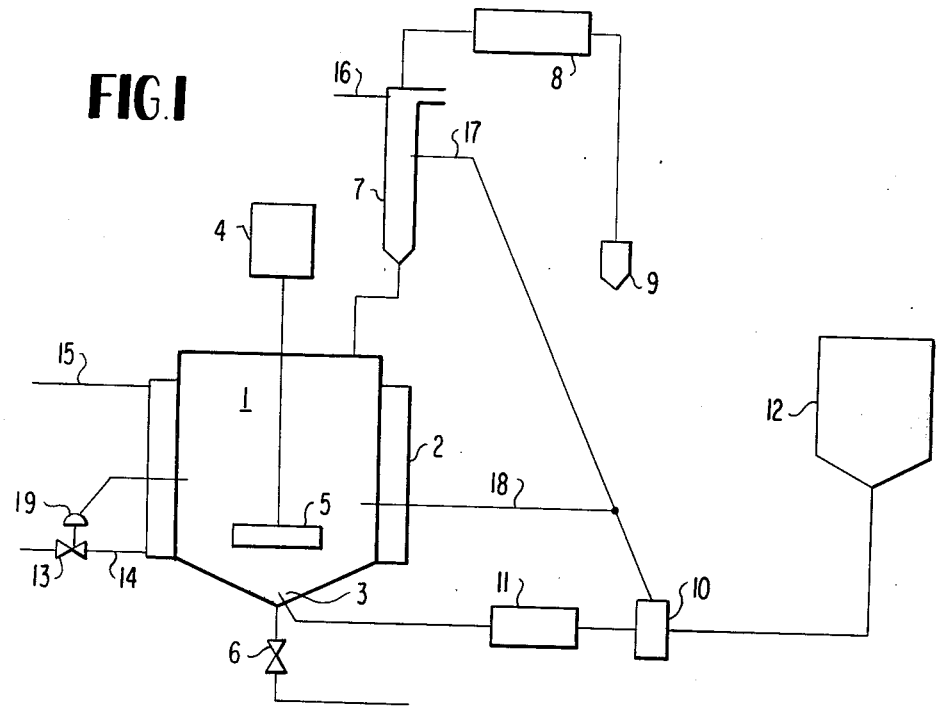
FIG. 1 is a schematic view of apparatus for preparing BHET in accordance with one embodiment of this invention.

According to the present invention, there is provided a process for preparing BHET which comprises suspending or dissolving terephthalic acid in molten liquid BHET at a temperature above the dew point of ethylene glycol and feeding gaseous or liquid ethylene glycol into the suspension to react it with the terephthalic acid, wherein the amount of ethylene glycol fed into the reactor is controlled so that the temperature inside a rectifying column is maintained at a temperature at which the ethylene glycol does not substantially distill off from the rectifying column and the partial pressure of the ethylene glycol is maximized.

As one skilled in the art will appreciate, the polyethylene terephthalate produced in accordance with the present invention can have varying molecular weights, and the molecular weights obtained in accordance with the present invention are in accordance with those conventionally obtained in the art. Generally, though not to be construed as limitative, the low molecular weight oligomers usually show a degree of polymerization on the order of 1 to about 10.

When ethylene glycol is fed in the liquid state, the requirement for maintaining the amount of ethylene glycol consumed at the stoichiometrically required amount is that the following thermal balance equation and material balance equation should both be met. The amount of heat required to heat ethylene glycol to its boiling point is ignored here because it is small as compared with the latent heat of evaporation of ethylene glycol and water.

Thermal balance $$UA(Tb - Ta) = V \cdot \gamma_1 + U \gamma_2 \quad \ldots (1)$$

Material balance $$V = \mu \quad \ldots (2)$$

wherein
U = the overall heat transmission coefficient of the jacket of the reactor [Kcal/m²·hr·deg],
A = the heat transmission area of the jacket of the reactor [m²],
Ta = the reaction temperature [°C.],
Tb = the temperature of the jacket [°C.],
V = the rate of feeding of ethylene glycol [moles/hr],
$\gamma_1$ = the latent heat of evaporation of ethylene glycol [Kcal/mole],
$\gamma_2$ = the latent heat of evaporation of water [Kcal/mole], and
$\mu$ = the rate of reaction (the rate of consuming terephthalic acid) [moles/hr].

It is known that, in such a reaction system, the rate of reaction is generally proportional to the partial pressure (Pe) of gaseous ethylene glycol. In order, therefore, to increase the rate of reaction (U), it is necessary to maximize the partial pressure (Pe) of ethylene glycol without causing the distillation of ethylene glycol from the top of the rectifying column. The rate of reaction under these conditions (Umax) is expressed by the following equations.

$$V = Umax \quad \ldots (3)$$

$$Tb = \frac{Umax (\gamma_1 + \gamma_2)}{UA} + Ta \quad \ldots (4)$$

In these equations, $\gamma_1$ and $\gamma_2$ are known, and Umax depends on the partial pressure (Pe) of ethylene glycol. On the other hand, UA can be determined if only what apparatus is to be used is decided. Hence, the optimal jacket temperature (Tb) can be obtained if Ta is determined.

Some embodiments of the present invention are described below in detail with reference to the accompanying drawings.

Referring to FIG. 1, the reference numeral 1 represents a reactor; 2, a heating jacket; 3, a feed opening for ethylene glycol; 4, a stirring motor; 5, a stirring vane; 6, an exhaust valve; 7, a rectifying column; 8, a condenser; 9, a receiver; 10, a feed pump; 11, a preheater for ethylene glycol; 12, a storage tank for ethylene glycol; 13, a valve for controlling a heat transfer medium; 14, an inlet opening for the heat transfer medium; 15, an outlet opening for the heat transfer medium; 16, a device for indicating the temperature at the top of the rectifying column; 17, a control device for detecting the temperature inside of the rectifying column and controlling the rate of feed of ethylene glycol; 18, a reaction temperature flow rate controlling device; and 19, a control device for controlling the amount of the heat transfer medium, for example, a mixture of biphenyl and biphenyl oxide, steam, etc., according to the temperature inside of the reactor.

In operation, the reactor 1 is charged with BHET and terephthalic acid, and a heat transfer medium is fed into the heating jacket 2 from the inlet opening 14. The inside of the reactor 1 is heated. The reactor 1 may be charged with a catalyst such as calcium acetate or manganese acetate, a stabilizer such as phosphoric acid or triphenyl phosphate, or a pigment such as titanium oxide or carbon black. When the temperature inside of the reactor 1 rises and the temperature of the reaction mixture reaches a predetermined reaction initiating temperature above the dew point of ethylene glycol at the pressure employed, ethylene glycol is fed into the reactor 1 from the storage tank 12 by means of the feed pump 10. Usually, this reaction initiating temperature $T_i$ is set at a point equal to the reaction temperature T or about 1° to about 20° C. lower than the reaction temperature T, and is usually about 197° C. or greater. At this time, the ethylene glycol is preheated by the preheater 11 so that it becomes gaseous prior to feeding it to the reactor 1. Since the temperature inside the reactor 1 is higher than the boiling point of ethylene glycol, when ethylene glycol is fed in the liquid state, the latent heat of evaporation due to the evaporation of ethylene glycol causes an abrupt decline in the temperature inside the reactor 1. Thus, if the heat transmitting ability of the jacket 2 is not sufficient, the heat transmission cannot catch up with the temperature decrease caused by evaporation, and the heat transmitting ability of the jacket cannot compensate for such a temperature drop. Hence, the preheating is required. When the jacket 2 has a sufficient heat transmission ability, such a preheating of ethylene glycol is not necessary, and the direct feeding of liquid ethylene glycol into the reactor 1 causes no problems.

When the reaction begins in this manner, the temperature inside of the reactor 1 is detected by the reaction temperature-flow rate control device 18, and the rate of feeding of the ethylene glycol is controlled so that the temperature inside the reactor becomes equal to the reaction temperature T. At the same time, the temperature of the top of the rectifying column 7 is detected by the temperature indicating device 16, and the controlling conditions of the temperature control device 17 are determined so that the column top temperature detected becomes near to but lower than the temperature at which ethylene glycol begins to distill off from the top of the rectifying column and is maintained at that temperature.

The amount of the ethylene glycol fed to the reactor 1 is controlled on the basis of the conditions for controlling the temperature inside the rectifying column. This controlling method is based on the fact that the temperature of the column top can be estimated from the temperature inside the column which has a certain relationship to the column top temperature. Thus, in the present invention, the feed rate of ethylene glycol is controlled on the basis of the temperature inside the rectifying column instead of the column top temperature. The reason why the above controlling method is employed in the present invention is that if the amount of ethylene glycol fed is controlled after detecting the column top temperature, the consequent time delay makes it extremely difficult to prevent the distillation off of ethylene glycol. Hence, the position of detecting the column inside temperature is desirably located as remote from the column top as possible so long as it permits an accurate estimate of the column top temperature.

It is sufficient, therefore, to operate the column top temperature indicating device 16 only when the relationship between the column top temperature and the column inside temperature to be detected in determined at the beginning of the reaction operation. Desirably, the temperature of the top of the rectifying column 7 is maintained at about 100° to about 120° C., most especially from 100° to 110° C. Since the temperature of the inside of the rectifying column varies according, for example, to the position of temperature detection or the capability of the rectifying column, it is preferable to determine the temperature after obtaining the relationship between the temperature inside and the column top temperature at the beginning of the operation in the manner mentioned above. Thus, generalization of the temperature range of the inside of the rectifying column is difficult. However, when the position of detection is a point about ⅛ to about 1/5 of the rectifying column height below the top the rectifying column, the temperature is usually appropriately set for the inside of the rectifying column to be about 110° to about 160° C., preferably 120° to 140° C.

When the inside temperature of the rectifying column has reached the upper limit of the controlled temperature thus determined, the feed pump 10 is controlled to stop or reduce the supply of ethylene glycol. When the supply of ethylene glycol to the reactor 1 is stopped or reduced, the inside temperature of the rectifying column drops. On the other hand, when the column inside temperature has reached the lower limit of the controlled temperature determined in the above-mentioned manner, the control device 17 again works to actuate the feed pump 10 and thereby resume feeding ethylene glycol or increase the amount of ethylene glycol fed to its original value.

The lower limit of the column inside temperature controlled is set at a point 0° to about 5° C. lower than the upper limit of the controlled temperature. It should be noted that this maximum 5° C. temperature difference is not overly critical, i.e., this value was determined on the basis of experience in running the process. However, as one skilled in the art will appreciate, if the temperature difference is larger, efficiency tends to be lowered, therefor, a broad temperature difference is disadvantageous. When the difference between the upper limit and the lower limit is 0, the controlling is a "one point on-off control". Since the temperature of the ethylene glycol fed into the reactor 1 is generally lower than the reaction temperature, the feeding of ethylene glycol tends to cause a decline in the temperature of the inside of the reactor 1. The inside temperature of the reactor 1 is controlled so as to avoid an excessive rise in the reaction temperature which will occur when the supply of ethylene glycol is stopped or reduced as described above. Thus, ethylene glycol can be fed while maintaining the inside temperature of the reactor 1 constant, and, therefore, the supply of ethylene glycol can be made dependent only on the temperature conditions within the rectifying column 7. This makes it possible to minimize the amount of the ethylene glycol fed.

It is necessary that the reaction temperature be maintained at about 197° to about 300° C., preferably 240° to 280° C. The temperature to which the inside temperature of the reactor 1 is to be adjusted cannot be given in general terms because it differs according to the heat-transmitting ability of the heating device. However, usually, it is appropriate to set it at a point 0° to about 10° C. higher than the reaction temperature, preferably 0° to 5° C. higher than the reaction temperature. Discussing this point in somewhat greater detail, temperature is generally established by considering the reaction temperature and the heat conducting capability of the jacket around the reactor. If the reaction temperature is set at a minimum required temperature and the heating jacket is set at an identical temperature, heat transferred from the jacket, is of course, not theoretically perfect, and since the reaction is an endothermic reaction, the reactor temperature will be lower than the reaction temperature. Accordingly, in the case the reaction temperature is set at the minimum temperature required or the heat conduction capability of the jacket is relatively small, the heating temperature must be set at a higher temperature than the reaction temperature. On the other hand, if the reaction temperature is set at the maximum temperature desired, the interior jacket of the reactor is always in the proper reaction range unless, of course, heat conduction capability of the jacket is extremely low. As one skilled in the art will appreciate, such a jacket would never be selected on a commercial basis.

As will be understood from the foregoing description, it is most efficient to operate the reaction temperature-flow rate control device 18 from the start of the reaction until the reaction reaches steady state, and to stop its operation after the reaction has reached the steady state. However, when the inside temperature of the reactor 1 temporarily decreases due to some factor in a system designed in the manner mentioned above, the amount of ethylene glycol vapor fed to the rectifying column also decreases and the inside temperature of the rectifying column 7 drops. Consequently, control device 17 works to continue the feeding of ethylene glycol to the reactor 1, and thereby to decrease the inside temperature of the reactor 1 further. In such a situation, therefore, the system might not be able to return easily to the desired operating range. This situation occurs when the heating jacket 2 does not possess sufficient heat transmitting ability and the control of the inside temperature of the reactor 1 cannot catch up with the temperature decrease. When the heat transmitting ability of the heating jacket 2 is sufficient, there is no such a problem. Hence, when the heating jacket 2 does not possess a sufficient capability to transmit heat, it is desirable from the standpoint of the stability of the system to operate the reaction temperature-flow rate control device 18 even after the reaction has reached steady state. In case the control device 18 is still operated after the reaction has reached steady state, the temperature at which the control device 18 is initiated is set at a point lower than the temperature at which the control device 19 is initiated. Accordingly, the reaction temperature-flow rate control device 18 does not normally operate, and the feeding of ethylene glycol depends only on the temperature conditions within the rectifying column 7. Thus, in this case, the amount of ethylene glycol fed can be minimized also.

As will be seen from the foregoing description, the system in accordance with the above-described embodiment of this invention has the advantage that even when the operating conditions deviate from the preferred range, the system returns itself to the preferred operating range.

The permissible amount of ethylene glycol that distills out is determined from the standpoint of economy and pollution control, and depends upon exterior conditions. It is difficult therefore to set a general limitation on the amount. Clearly, however, it is desirable that the amount be as small as possible, and usually amounts in excess of about 2 to about 3% are undesirable.

Figure 2:
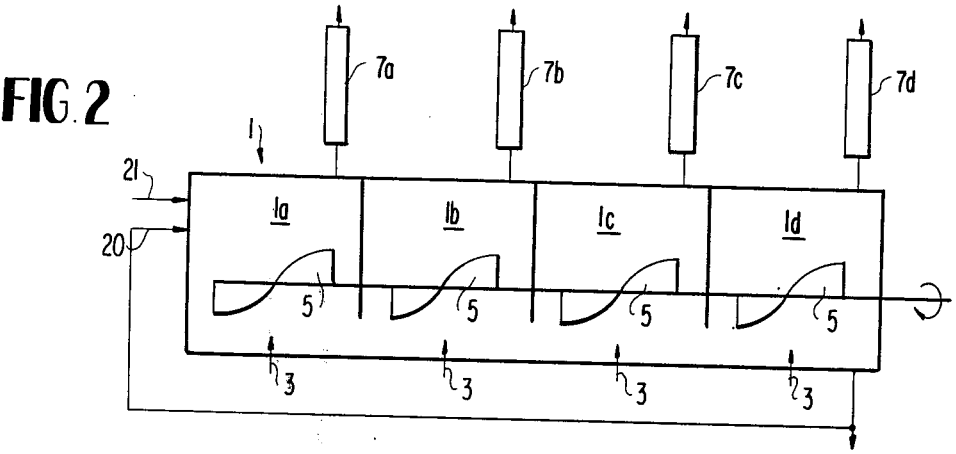
FIG. 2 is a flowsheet showing another embodiment of the present invention.

FIG. 2 shows another embodiment of the present invention.

In FIG. 2, the reactor 1 is a horizontal reactor partitioned into four chambers 1a, 1b, 1c and 1d, and rectifying columns 7a, 7b, 7c and 7d are provided corresponding to chambers 1a, 1b, 1c and 1d. Ethylene glycol is fed into each of chambers 1a, 1b, 1c and 1d. The amount of the ethylene glycol fed is controlled in the same way as in the aforesaid embodiment with respect to each of chambers 1a, 1b, 1c and 1d so that the ethylene glycol will not distill out from the top of each of the rectifying columns 7a, 7b, 7c and 7d. Since the manner of control was the same as shown in FIG. 1, the control means for the feed rate is not shown in FIG. 2.

The resulting BHET is fed to a polycondensation reaction apparatus, and a part of it is recycled to the first reaction chamber 1a through feed opening 20. Terephthalic acid is continuously fed into the first reaction chamber 1a from feed opening 21. The apparatus in this embodiment is substantially a continuous reaction apparatus. Since the recycling of BHET is for the purpose of increasing the flowability of the system, it is permissible to feed a separate supply of BHET without resorting to recycling, if desired. Other numerals have the same meaning as in FIG. 1.

Figure 3:
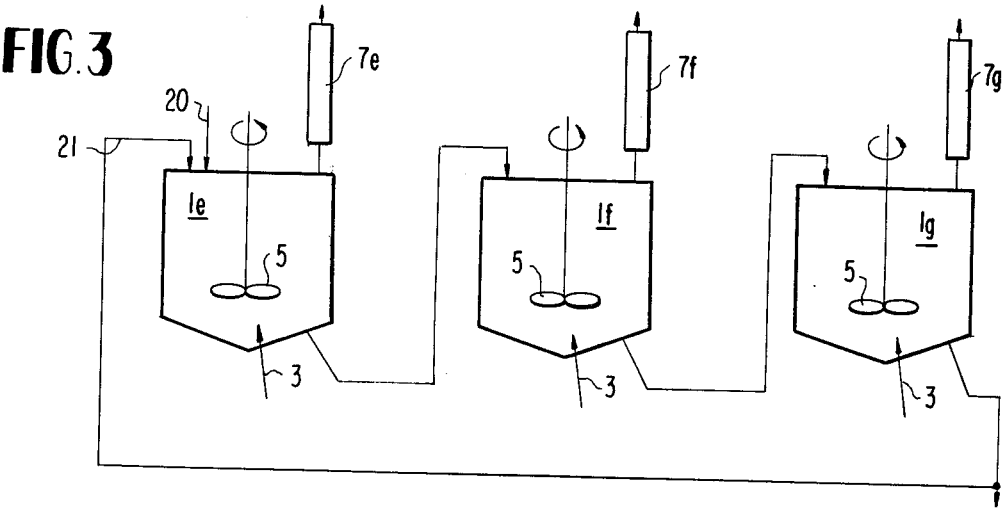
FIG. 3 is a flowsheet showing still another embodiment of the present invention.

FIG. 3 shows still another embodiment of the present invention.

In FIG. 3, a plurality of reactors 1e, 1f and 1g are provided in series. Rectifying columns 7e, 7f and 7g are provided to the reactors 1e, 1f and 1g, respectively. Ethylene glycol is fed to each of the reactors. The amount of the ethylene glycol fed is controlled in the same way as in FIG. 1 with respect to each of the reactors 1e, 1f and 1g so that the ethylene glycol will not distill out from the top of each of the rectifying columns 7e, 7f and 7g. Since the manner of control was the same as shown in FIG. 1, the control means for the feed rate is not shown in FIG. 3. Other numerals have the same meaning as in FIG. 2.

Recycling of the BHET and the continuous feeding of terephthalic acid are performed in the same way as in FIG. 2.

The embodiments shown in FIGS. 2 and 3 have the advantage that the total volume of the reactors can be reduced and the quality of the product can be made uniform, but somewhat increased installation costs are involved.

Needless to say, it should be noted that the present invention is not limited to the embodiments described above, but can be modified in various ways within the scope of the invention set forth in the appended claims.

For example, the heating of the reactor is not necessarily carried out by a jacket, but other known methods of heating, for example, by means of a heating coil, can be employed. Furthermore, the number of chambers in the reactor of FIG. 2 is not limited to four, and the number of reactors in FIG. 3 is not limited to three.

According to the present invention, BHET can be produced effectively while inhibiting the distillation of ethylene glycol. Accordingly, the amount of ethylene glycol consumed can be reduced to the stoichiometrically required amount. As a result, heat losses can be reduced, and apparatus for recovering and purifying ethylene glycol and facilities for disposing of wastes become unnecessary. Hence, BHET can be produced at low cost.

The above disclosure will enable one skilled in the art to practice the invention, and in general includes description regarding the best modes contemplated of practicing the present invention. However, as with any process invention, on a commercial scale certain most highly preferred conditions exist, and these are set out below.

During the process of the present invention the ratio of terephthalic acid/BHET is generally maintained at 2.5 or less, more preferably 1.5 or less, and most preferably about 1 (molar ratio). The temperature of the interior of the reactor is, of course, maintained at substantially equal to the reaction temperature and, further, the temperature at the top of the rectifying column is maintained at about 100° to about 120° C., more preferably 100° to 110° C., in combination with setting the temperature at the inside of the rectifying column at about 110° to about 160° C., more preferably 120° to 140° C. The reaction is conveniently conducted at normal pressure.

In order to illustrate the effects of the present invention further, the following Comparative Example and Examples are provided. Unless otherwise indicated, in the Comparative Examples the temperature in the inside of the rectifying column was 197° C. (without control), the degree of polymerization of the products was about 1 to 10, and in Examples 1 to 3 the temperature of the inside of the rectifying column was 100° to 120° C. (control). Further, in Examples 1 to 3, the control was essentially a "one point on-off" control; hence, the temperature range of the control was 0.

COMPARATIVE EXAMPLE

A rectifying column consisting of a glass tube with a length of 300 mm and a diameter of 25 mm with a stainless steel gauze packing therein was attached to a glass reactor consisting of a 500 ml. three-necked flask, and the following reaction was performed at atmospheric pressure without controlling the temperature of the inside of the rectifying column.

First, 178 g of BHET was charged into the glass reactor, and melted in an atmosphere of nitrogen. Further, 166 g of terephthalic acid was added. While controlling the inside temperature of the reactor so that the reaction mixture was maintained at 240° C., ethylene glycol in liquid state was fed without preheating so that the reaction mixture was maintained at 240° C., and reacted. The reaction ended in 3.5 hours to give pure white BHET.

The amount of by-product diethylene glycol in the product was 0.8 mole %, and the amount of the ethylene glycol consumed was 157 ml. The amount of the distillate from the rectifying column was 108 ml. The distillate consisted of 65% by weight of ethylene glycol, the remainder being substantially water.

EXAMPLE 1

The procedure of the Comparative Example 1 was repeated using the same reaction apparatus under the same reaction conditions except as noted below. The temperature inside of the rectifying column was detected at a point ¼ below the top of the rectifying column (¼ of the height), and the temperature inside of the rectifying column was controlled by a "one point on-off control" process so that the temperature detected was 120° C.

The reaction ended in 3.5 hours to yield pure white BHET. The amount of by-product diethylene glycol in the product was 0.8 mole %, and the amount of ethylene glycol consumed was 70 ml. The amount of the distillate from the rectifying column was 23 ml. The distillate consisted of 0.7% by weight of ethylene glycol, the remainder being substantially water.

The results obtained demonstrate that, in this example, the amount of the distillate was reduced and the content of the ethylene glycol in the distillate could also be reduced markedly as compared to the Comparative Example described above.

EXAMPLE 2

The procedure of Example 1 was repeated except that the reaction temperature was changed to 280° C.

The reaction ended in 1.5 hours to provide pure white BHET. The amount of by-product diethylene glycol in the product was 0.9 mole %, and the amount of the ethylene glycol consumed was 71 ml. The amount of the distillate was 25 ml, and the distillate consisted of 0.8% by weight of the ethylene glycol the remainder being substantially water.

EXAMPLE 3

A packed rectifying column having a diameter of 22 cm and a height of 75 cm (packed with ⅜ inch Raschig rings) was attached to a 30 l stainless steel reactor, and the following reaction was carried out at atmospheric pressure.

First 10.0 Kg of BHET was charged into the reactor and melted in an atmosphere of nitrogen, and 10.0 Kg of terephthalic acid was added. While controlling the inside temperature of the reactor so as to maintain the temperature of the reaction mixture at 255° C., ethylene glycol was fed in vapor state after being pre-heated to 200° C., and the reaction was carried out.

The temperature inside of the rectifying column was detected at a point ⅛ from the top of the column (⅛ of the height below the top), and controlled by a "one point on-off control" process so that the temperature detected became 120° C.

The reaction ended in 2.5 hours to yield pure white BHET. The amount of by-product diethylene glycol in the product was 0.9 mole %, and the amount of ethylene glycol consumed was 5400 ml. The amount of the distillate from the rectifying column was 1800 ml, and the distillate consisted of 1.1% by weight of ethylene glycol, the remainder substantially water.

While the invention has been described in detail and with reference to specific embodiments thereof, it will be apparent to one skilled in the art that various changes and modifications can be made therein without departing from the spirit and scope thereof.

What is claimed is:

1. A process for preparing BHET in a reactor provided with a rectifying column which comprises:
   (i) suspending or dissolving terephthalic acid in a molten liquid of BHET at a temperature above the dew point of ethylene glycol;
   (ii) feeding gaseous or liquid ethylene glycol into the suspension or the solution in said reactor to react it at a temperature of about 197° to about 300° C. with the terephthalic acid, wherein the feeding of ethylene glycol to the reactor is controlled so that the temperature inside of and at a position at the top of the rectifying column is maintained at about 100° to about 120° C. at which more than about 3% of the ethylene glycol does not distill off from the rectifying column and the partial pressure of the ethylene glycol is maximized, said control being maintained by
   (iii) discontinuing feeding of the ethylene glycol when the temperature at a position about ⅛ to about 1/5 below the top of the rectifying column rises to a temperature within the range of about 110° C. to about 160° C.; and
   (iv) continuing feeding of the ethylene glycol when the temperature at said position about ⅛ to about 1/5 below the top of the rectifying column falls to 0° to about 5° C. lower than the temperature point in step (iii).

2. The process of claim 1, wherein the molar ratio of terephtalic acid to BHET is maintained at about 2.5 or less.

3. The process of claim 2, wherein the said molar ratio is 1.5 or less.

4. The process of claim 2, wherein the temperature inside of and at a position at the top of the rectifying column is maintained at 100° to 110° C.

5. The process of claim 2, wherein the temperature of the reaction is 240° to 280° C.

6. The process of claim 1, wherein the temperature at the position about ⅛ to about 1/5 below the top of the rectifying column in step (iii) is 120° to 140° C.

* * * * *